United States Patent
Digioia

(10) Patent No.: US 10,421,925 B2
(45) Date of Patent: Sep. 24, 2019

(54) PROCESS FOR THE OXIDATIVE CLEAVAGE OF VICINAL DIOLS

(71) Applicant: NOVAMONT S.P.A., Novara (IT)

(72) Inventor: Francesca Digioia, Barengo (IT)

(73) Assignee: NOVAMONT S.P.A., Novara (IT)

( * ) Notice: Subject to any disclaimer, the term of this patent is extended or adjusted under 35 U.S.C. 154(b) by 0 days.

(21) Appl. No.: 16/306,122

(22) PCT Filed: Jun. 5, 2017

(86) PCT No.: PCT/EP2017/063613
§ 371 (c)(1),
(2) Date: Nov. 30, 2018

(87) PCT Pub. No.: WO2017/211762
PCT Pub. Date: Dec. 14, 2017

(65) Prior Publication Data
US 2019/0136150 A1 May 9, 2019

(30) Foreign Application Priority Data
Jun. 6, 2016 (IT) .................. 102016000057624

(51) Int. Cl.
*C11C 3/00* (2006.01)
*C07C 67/31* (2006.01)
*C07C 67/333* (2006.01)
*C07C 51/245* (2006.01)
*C07C 51/367* (2006.01)
*B01J 23/30* (2006.01)

(52) U.S. Cl.
CPC .............. *C11C 3/006* (2013.01); *B01J 23/30* (2013.01); *C07C 51/245* (2013.01); *C07C 51/367* (2013.01); *C07C 67/31* (2013.01); *C07C 67/333* (2013.01)

(58) Field of Classification Search
CPC ........ C11C 3/006; B01J 23/30; C07C 51/245; C07C 67/31
USPC ......................................................... 554/121
See application file for complete search history.

(56) References Cited

FOREIGN PATENT DOCUMENTS

| WO | WO-2011/080297 A1 | 7/2011 | |
|----|----|----|----|
| WO | WO-2011080297 A1 * | 7/2011 | ........... C07C 51/245 |

* cited by examiner

*Primary Examiner* — Deborah D Carr
(74) *Attorney, Agent, or Firm* — Polsinelli PC

(57) ABSTRACT

This invention relates to a process for obtaining monocarboxylic and dicarboxylic acids from unsaturated carboxylic acids and/or their derivatives. The said process comprises an oxidative cleavage reaction of vicinal diols into which are fed at least some of the aqueous phase separated out at the end of the reaction itself and at least one base so that the pH of the aqueous solution at the start of the oxidative cleavage reaction is between 4 and 7.

20 Claims, 3 Drawing Sheets

Flow diagram of the process according to the invention.

FIGURE 1: Flow diagram of the process according to the invention.
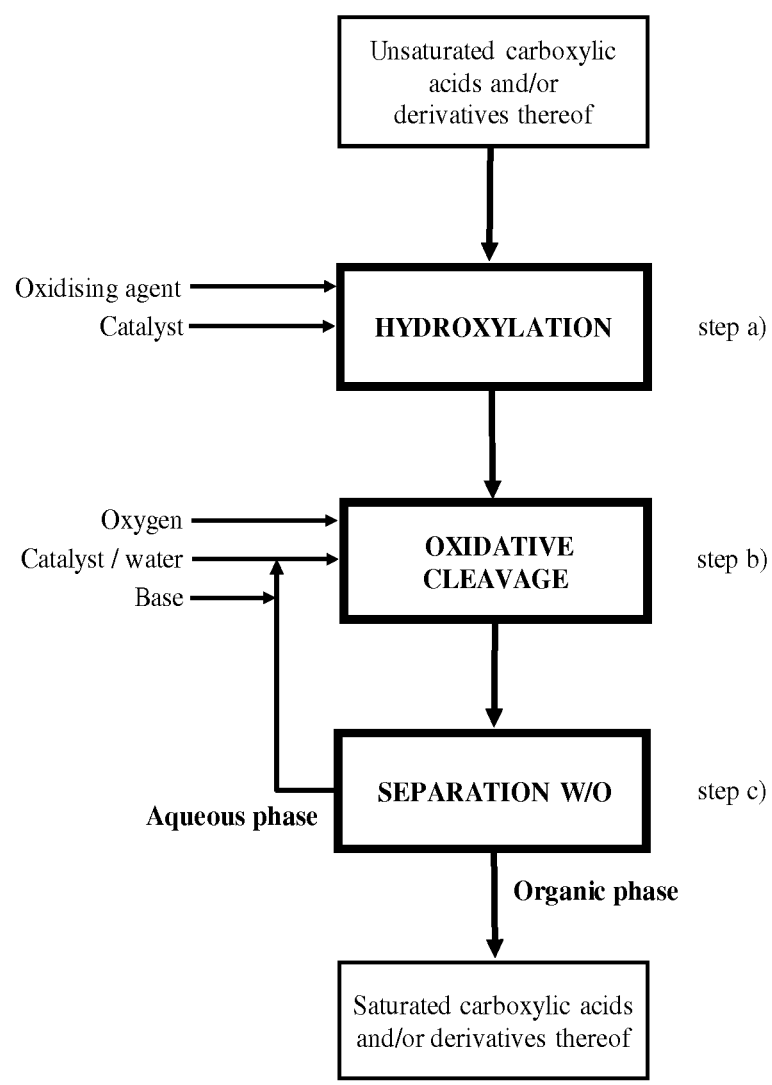

FIGURE 2: Absorption of oxygen (l/kg of oil) during the oxidation of step b) carried out by recycling 100% of the aqueous phase containing the catalyst, without the addition of base (Example 1 comparative) and with addition of base according to the invention (Example 2).
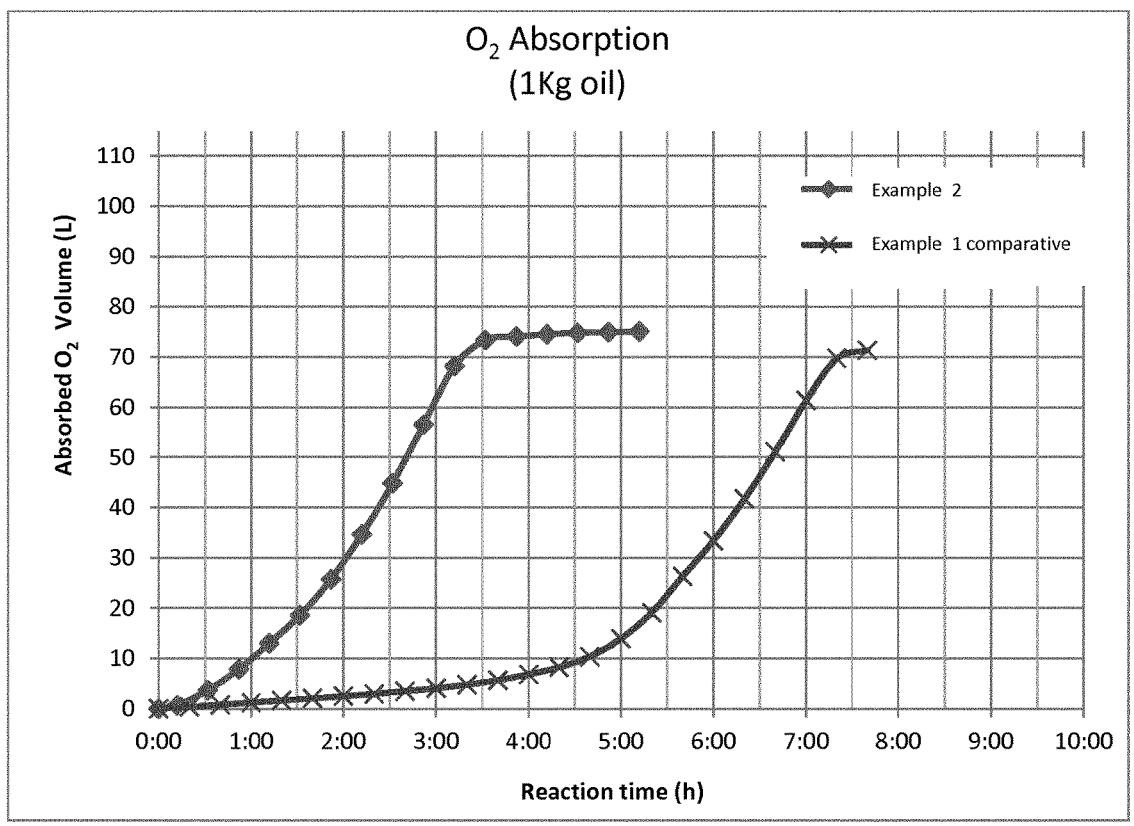

FIGURE 3: Absorption of oxygen (l/kg of oil) during the oxidation of step b) carried out by recycling 60% of the aqueous phase containing the catalyst, without the addition of base (Example 4 comparative) and with addition of base according to the invention (Example 3).
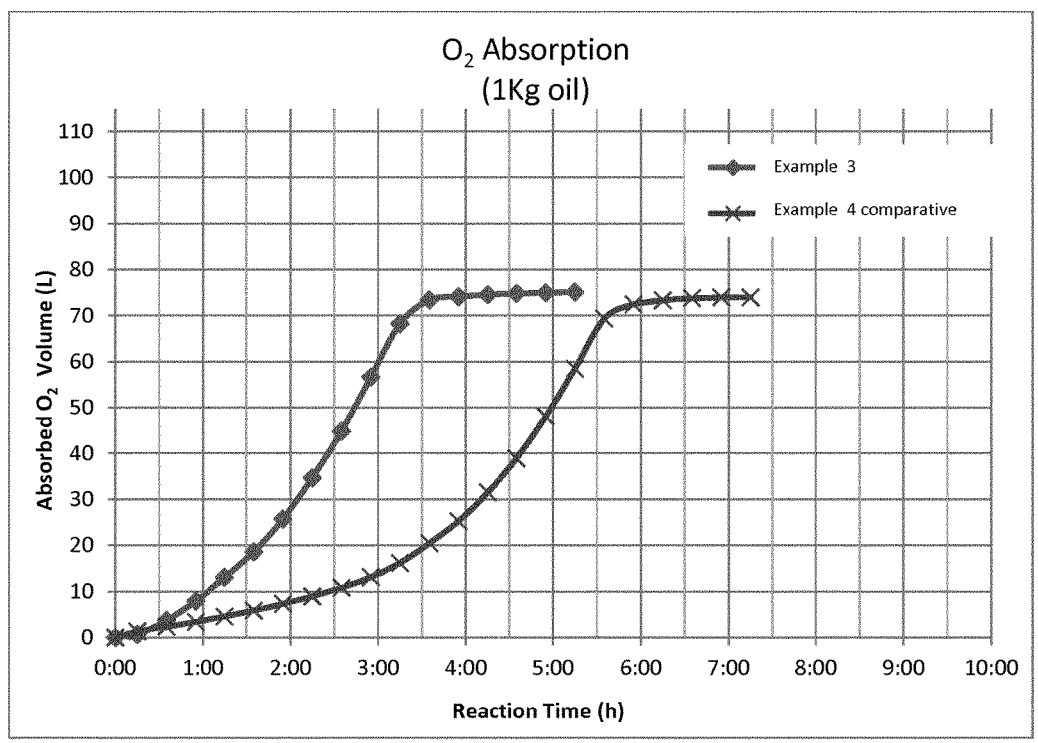

PROCESS FOR THE OXIDATIVE CLEAVAGE OF VICINAL DIOLS

CROSS REFERENCE TO RELATED APPLICATIONS

This application is the National Phase of Application No. PCT/EP2017/063613 filed Jun. 5, 2017, which claims priority to Application No. 102016000057624 filed in Italy on Jun. 6, 2016 under 35 U.S.C. § 119. The entire contents of each application are hereby incorporated by reference.

This invention relates to a process for obtaining carboxylic acids comprising an oxidative cleavage reaction of vicinal diols performed in the presence of at least one oxidising agent containing oxygen, water and at least one catalyst, characterised in that the pH value of the aqueous solution at the start of the reaction is between 4 and 7.

Processes providing for the oxidative cleavage of vicinal diols are described for example in EP 666 838 B1, EP 1 926 699, WO 2008/138892, WO 2011/080297 and WO 2011/080296. Through these processes carboxylic acids having one or more acid functional groups can be obtained continuously or in batch mode from unsaturated fatty acids, their derivatives or their natural sources, such as vegetable oils. The unsaturations present in such fatty acids undergo a first step of catalytic oxidation, which results in the production of vicinal diols; the two hydroxyl groups of the vicinal diols then undergo a second oxidation step which brings about the formation of monocarboxylic acids and dicarboxylic acids and typically requires the addition of a second catalyst, which is not the same as the first. From the point of view of industrial production the possibility of recovering and reusing such catalysts in the process, possibly following suitable treatments, represents an obvious advantage, both economic and environmental.

In addition to this, in the above mentioned processes, the catalyst for the first oxidation step is typically not removed from the reaction mixture before the second oxidation step is carried out. For example, in the process in application WO 2008/138892 both the catalysts are separated out from the oxidative cleavage product (the latter in the oily phase) in the aqueous phase only at the end of the second oxidation step. This aqueous phase containing the catalysts for both oxidation reactions can be reused to catalyse the second step, i.e. oxidative cleavage of the diol. However, it has been observed that this recycling results in a fall in the pH of the aqueous phase during the oxidative cleavage reaction, and a consequent slowing in the reaction rate, in addition to a reduction in the yield from it.

Conversely, with the process according to this invention, thanks to maintaining weakly acid pH conditions throughout the reaction of oxidative cleavage of the diol, and in particular in the presence of initial pH values of between 4 and 7, it is possible to reuse the catalytic solution separated out at the end of the said reaction, keeping the reaction time almost unchanged. It has also surprisingly been observed that reuse of the catalytic solution under these conditions improves the reaction yield in comparison with the use of fresh catalyst, not only in the case where the latter is partly substituted, but also in the case where it is wholly substituted. These effects occur even when the said reuse is repeated several times.

This invention therefore relates to a process of the oxidative cleavage of unsaturated carboxylic acids and/or their derivatives for the obtainment of saturated monocarboxylic and dicarboxylic acids or derivatives of dicarboxylic acids comprising the steps of:

a) reacting at least one unsaturated carboxylic acid or a derivative thereof, an oxidising compound and a catalyst capable of catalysing the oxidation reaction of the olefin double bond, in order to obtain an intermediate compound containing vicinal diols, and b) reacting the said intermediate compound, oxygen or compound containing oxygen, and a catalyst capable of catalysing the oxidation reaction of vicinal diols to carboxylic acid groups in the presence of water, obtaining an organic phase comprising saturated monocarboxylic acids and saturated dicarboxylic acids or derivatives thereof and an aqueous phase comprising the said catalyst and optionally the catalyst from step a), and c) separating the said aqueous phase from the said organic phase, characterised in that at least a part of the said aqueous phase separated out in step c) and comprising the catalyst and at least one base are fed to step b) so that the mixture of the intermediate compound of step a) with the said part of aqueous phase and the said base has a pH value of between 4 and 7.

FIG. 1 shows a flow diagram of the process in which the base is added to the aqueous phase (which has been separated from the organic phase in step c)) before being fed to step b).

FIG. 2 shows the absorption of oxygen (1/kg of oil) during oxidation of the vicinal diols from highly oleic sunflower oil (step b) carried out by recycling 100% of the aqueous phase separated out in step c), without the addition of base (Comparative Example 1) and with the addition of base (Example 2).

FIG. 3 illustrates oxygen absorption (1/kg of oil) during oxidation of the vicinal diols from highly oleic sunflower oil (step b) carried out by recycling 60% by weight of the aqueous phase separated out from step c), with the addition of base (Example 3) and without it (Comparative Example 4).

The process will now be described in greater detail.

According to an aspect, the invention relates the oxidation of unsaturated carboxylic acids (step a) of the process).

Unsaturated carboxylic acids which are suitable for use in aforesaid step a) are monounsaturated and/or polyunsaturated carboxylic acids such as, for example, 9-tetradecenoic (myristoleic) acid, 9-hexadecenoic (palmitoleic) acid, 9-octadecenoic (oleic) acid, 12-hydroxy-9-octadecenoic (ricinoleic) acid, 9-eicosenoic (gadoleic) acid, 13-docosenoic (erucic) acid, 15-tetracosenoic (nervonic) acid, 9,12-octadecadienoic (linoleic) acid, and 9,12,15-octadecatrienoic (linolenic) acid. Monounsaturated carboxylic acids are preferred; the use of oleic acid, from the oxidative cleavage of which are mainly obtained azelaic acid and pelargonic acid, is particularly advantageous.

Mixtures of unsaturated carboxylic acids, such as for example those present in vegetable oils such as soya oil, olive oil, castor oil, sunflower oil, peanut oil, maize oil, palm oil, jatropha oil, *cuphea* oil, Carduae oils such as *Cynara cardunculus, Silybum marianum* or *Carthamus tinctorius*, Brassicaceae oils such as *Crambe abyssinica, Brassica carinata, Brassica napus* (colza), *Lesquerella*, and other oils having a high monounsaturated acids content are also advantageously used as starting materials for this process.

According to another aspect, the invention relates the oxidation of derivatives of unsaturated carboxylic acids.

The term "derivative" refers to a carboxylic acid in which the carboxylic group is reacted so as to prevent or minimize any further reactions of this carboxylic group thus modified in the course of the process. For example, according to this invention, "derivative" of an unsaturated carboxylic acid means an unsaturated carboxylic acid in which the carboxylic acid group forms an ester bond (e.g. by reaction with an alcohol), an amide bond, a nitrile bond (e.g. by reaction with an amine), or a thioester bond (e.g. by reaction with a thiol), etc. The said derivatives may be of natural or synthetic origin. Ester derivatives are preferred.

In the case of derivatives of the ester type, the carboxylic acid group may be linked to monoalcohols or polyalcohols. Preferred monoalcohols comprise $C_1$-$C_9$ alkyl groups; methyl, ethyl, propyl and butyl alcohols are preferred. One example of a preferred polyalcohol is glycerol.

Methyl and ethyl esters of unsaturated carboxylic acids are particularly advantageous as starting materials for this process, in particular those obtained by the transesterification of methanol and ethanol with triglycerides present in sunflower oil having a high oleic acid content.

Monoglycerides, diglycerides and/or triglycerides of carboxylic acids, whether synthesised or natural, are also particularly advantageous as starting materials for this process. Triglycerides present in vegetable oils or their mixtures are particularly preferred. By vegetable oils are meant both the unmodified product from crushing, or oils which have undergone chemical or physical/chemical changes, such as, for example, purification or hydrogenation treatments or enzyme enrichment processes. Examples of preferred vegetable oils are: soya oil, olive oil, castor oil, sunflower oil, peanut oil, maize oil, palm oil, jatropha oil, *cuphea* oil, Brassicaceae oils such as *Crambe abyssinica, Brassica carinata, Brassica napus* (colza), Carduae oils such as *Cynara cardunculus* (thistle), *Silybum marianum, Carthamus tinctorius, Lesquerella*, and other oils having a high monounsaturated acids content. Particularly preferred is the use of sunflower oil and thistle oil.

The oxidising agent used to carry out step a) is selected from osmium tetroxide, permanganates, hydrogen peroxide, alkyl hydroperoxides and percarboxylic acids such as, for example, performic acid, peracetic acid or perbenzoic acid. The said oxidising agent is more preferably an aqueous solution of hydrogen peroxide in concentrations of between 30 and 80% by weight, preferably between 40 and 70%, and even more preferably between 49 and 65%.

The catalyst for step a) belongs to the group of transition elements. Fe, Mn, Mo, Nb, Os, Re, Ti, V, W, Zr and their acids, alkali metal salts and complexes are advantageously used as homogeneous or heterogeneous phase catalysts, possibly in supported or nanostructured form. The use of tungstic acid and/or its derivatives, such as phosphotungstic acid is particularly preferred. The said catalyst is present in quantities of between 0.03% and 3% in moles, preferably between 0.05% and 1.8% in moles, and even more preferably between 0.06% and 1.5% in moles with respect to the total moles of unsaturations.

The diol resulting from step a) is caused to react—in step b)—with oxygen or an oxidising compound containing oxygen. The use of air is particularly advantageous. Air enriched with oxygen may also be used.

As far as the catalyst for step b) of oxidative cleavage is concerned, this belongs to the group of transition elements. Ce, Cr, Co, Cu, Mn, Mo, Re, Os, V and W and their acids, alkali metal salts and complexes, are advantageously used as homogeneous phase catalysts. The use of cobalt salts such as, for example, acetate, chloride, sulfate, bromide and nitrate, used in quantities between 0.05% and 3% in moles, preferably between 0.1% and 2% in moles and even more preferably between 0.3% and 1.5% in moles with respect to the diol produced in step a), are particularly preferred. Particularly preferred is the use of cobalt acetate and cobalt chloride.

At the start of step a) a small quantity of the intermediate compound obtained at the end of step a) itself may be added, as the diols present in it encourage activation of the reaction. The said intermediate compound may be added in a quantity of ≤5%, preferably ≤3% by weight with respect to the starting oil.

Advantageously, during the course of step a) of the process according to the invention, air or an inert gas (e.g. nitrogen) are caused to flow in order to remove part of the water produced in the process. Excessive dilution of $H_2O_2$ is avoided in this way. An alternative to the flow of these gases is evaporation under vacuum.

The reaction temperatures for step a) and step b) advantageously lie between 45 and 95° C., preferably between 50 and 90° C. In particular, the reaction temperature in step a) is advantageously between 55 and 80° C., while the reaction temperature in step b) is advantageously between 55 and 90° C., even more advantageously between 60 and 80° C.

Advantageously, when carrying out both step a) and step b) of this process, the reaction time (that is the average residence time in the reactors in the case of a continuous process) is between 2 and 8 hours for each step.

The reaction time for step b) is preferably between 2 and 6 hours. In the known processes, the recycling—or partial recycling—of the catalyst in the aqueous phase slows down the oxidative cleavage reaction, with a consequent increase in reaction time. In the process according to this invention instead, even all the catalyst in step b) can be recycled without altering the reaction time.

"Reaction time" means, according to this invention, the time occurring between the start and end of oxygen absorption during the oxidative cleavage reaction. Oxygen absorption is measured as the difference between the quantity of oxygen delivered to the reactor—or reactors—in step b) and the quantity of oxygen leaving them; these quantities can, for example, readily be measured by oxygen meters located at the reactor's gas inlet and outlet.

In a preferred embodiment of the process, the intermediate product resulting from step a) containing vicinal diols is fed directly to the reactor in which step b) is carried out, with the effect of an advantageous decrease in reaction time, thanks to the greater reactivity of the intermediate product itself, together with a significant increase in reaction yield.

Steps a-b) of the process may advantageously be carried out at atmospheric pressure or, in any event, moderate oxygen partial pressures, with obvious advantages from the point of view of industrial production.

Step a) is preferably carried out at atmospheric pressure or under vacuum.

Step b) is preferably carried out with air at a pressure of ≤50 bar, preferably ≤30 bar.

According to one aspect of the invention, these steps a-b) are carried out in continuous reactors. The use of such continuous reactors makes it possible to reduce reaction volumes, aiding the exchange of heat. In a preferred embodiment, one or more reactors of the CSTR (Continuous Stirred-Tank Reactor) type, possibly placed in series, are used.

Continuous reactors of the gas/liquid type are advantageously used in step b). External recirculation (Loop CSTR) reactors, which encourage contact between the oxidising agent in the gaseous phase and the reaction mixture in the liquid phase, are preferably used when the oxidizing agent is air.

Both steps a) and b) are preferably carried out without the addition of organic solvents.

The intermediate product obtained from step a) is fed to step b), where it is caused to react with oxygen or a compound containing oxygen, without the need for any purification treatment or removal of the catalyst.

The ratio by weight between the aqueous phase and the organic phase during step b) is advantageously below 5:1 and preferably less than or equal to 3:1.

According to a preferred embodiment of the invention, vegetable oils comprising triglycerides of unsaturated fatty acids are used as starting material and the ratio by weight between the aqueous phase and the organic phase during step b) is kept less than or equal to 1:1. Preferably, in this case such a ratio by weight is kept below or equal to 1:3 throughout the oxidation reaction in step b). According to a more preferred aspect of the process, step b) is carried out without the addition of water, apart from that in which the catalyst is dissolved.

As far as the pH value of the aqueous component of the reaction mixture is concerned, when measured after addition of the oxidative cleavage catalyst at the intermediate compound obtained in step a (i.e. before the beginning of step b), it is preferably equal to or lower than 7. Preferably the said value will be 4 or above and below 7, for example between 4 and 6.5 or between 4 and 5.5.

The value of the final pH of the aqueous phase measured at the end of step b) is instead typically between 2.5 and 3.5. The oxidative cleavage reaction in step b) in fact gives rise to the formation of carboxylic acids, the dissolution of which in the aqueous phase can give rise to a change in pH, together with a possible presence of soluble forms of the catalyst used in step a).

According to a more preferred embodiment of this process in which tungstic or phosphotungstic acids are used as the catalyst in step a) and an aqueous solution of a cobalt salt as catalyst in step b) (e.g. cobalt acetate), the pH value of the aqueous catalytic solution fed to step b) is preferably between 6 and 8. Thus, following contact between that aqueous catalytic solution and the intermediate product obtained in step a), the aqueous phase before step b) has a pH which is advantageously greater than or equal to 4.

At the end of step b) of the process according to the invention the aqueous phase is separated from the organic phase (step c). This operation is carried out in accordance with practices known to those skilled in the art, for example, by means of decanting or centrifuging.

Typically said step c) comprises at least one decanting operation, at temperatures of preferably between 60 and 90° C., more preferably between 75 and 90° C., and at a pressure close to atmospheric (approximately 1 bar).

Separation step c) also preferably comprises one or more operations selected from degassing, heating, filtration, washing with water in addition to that fed in during the reactions in steps a) and b), and/or added with suitable quantities of organic solvents which are immiscible with water. These operations have the effect of assisting separation of the aqueous phase from the organic phase.

Examples of solvents suitable for assisting separation of the aqueous phase from the organic phase are hydrocarbons such as hexane, octane, nonane or mixtures thereof.

The addition of octane in quantities below 15% and over 5% by weight, preferably below 12% and over 8% by weight, with respect to the weight of the oxidation product (i.e. organic phase together with aqueous phase) is particularly advantageous.

According to a preferred aspect of the process, the aqueous phase is separated out after degassing, addition of organic solvent and subsequent decanting.

The operation of separating the two phases may be carried out one or more times, possibly with adding fresh water and performing one or more successive washes of the separated organic phase, for example counter-currently.

The aqueous phases resulting from any washing operations in the course of step c), containing the catalyst from step b) and optionally the catalyst from step a), are advantageously pooled and optionally undergo preliminary treatments before being again fed to step b) of the process according to the invention.

The said preliminary treatments comprise, for example, concentration, which may be carried out by any method known to those skilled in the art, for example through evaporation of the solvent water, through simple heating and/or under vacuum, or by using variable porosity membranes (e.g. microfiltration, ultrafiltration, reverse osmosis). The said operation is typically performed in the case where the washing waters are pooled in order to restore the oxidative cleavage catalyst to its optimum concentration.

Together with the aqueous phase separated out in step c) of the process, at least one base is added again to step b) so as to obtain weakly acid pH conditions at the start of the oxidative cleavage reaction.

Suitable bases are, for example, bases capable of increasing the pH of the aqueous solution separated out at the end of step c), such as, for example, alkali metal, alkaline earth and transition metal hydroxides (e.g. sodium hydroxide, potassium hydroxide, calcium hydroxide, magnesium hydroxide, cobalt hydroxide), alkaline earth oxides (e.g. calcium oxide, magnesium oxide), alkali metal and alkaline earth carbonates and bicarbonates (e.g. calcium carbonate, sodium carbonate, sodium bicarbonate, basic magnesium carbonate), or acetates. Preferred examples are strong bases such as sodium hydroxide or potassium hydroxide.

The said base may be fed to step b) separately with respect to the aqueous phase separated out from step c) or added thereto before feeding to the reactor or reactors in step b).

The said base may be fed to step b) in for example, solid form, or in the form of an aqueous solution. Those skilled in the art will be readily able to determine the amount of base which has to be added to achieve the desired pH at the start of step b), according to the amount and initial pH of the said aqueous phase, the selected base and the operative conditions (e.g. continuous or batch process).

According to a preferred aspect of the process, the said base is added, preferably in the form of an aqueous solution, to the aqueous phase before feeding to step b).

A particular advantage of the invention lies in the minimum amount of base needed to obtain the desired pH value when derivatives of unsaturated carboxylic acids, such as methyl esters or triglycerides of unsaturated fatty acids, are used as starting material for the process.

The aqueous phase resulting from step c) may be fed to step b) together with the feed of fresh catalyst for step b) (partial replacement of the oxidative cleavage catalyst) or as an alternative to the latter (total replacement).

In the case of partial replacement of fresh catalyst, this may be carried out in any ratio by weight between fresh catalyst and recycled catalyst (i.e. originating from step c) of the same process), keeping the total quantity of catalyst present unchanged in relation to the total moles of diol. For example, a quantity of aqueous phase resulting from step b) containing up to 1%, 5%, 10%, 20%, 30%, 40%, 50%, 60%, 70%, 80% or 90% by weight of recycled catalyst with respect to the total weight of catalyst, may be fed to step b). In the case where more of the fresh catalyst is replaced, the aqueous phase which is fed to step b) preferably contains all the catalyst from step b) separated out in the aqueous phase at the end of step c).

In a preferred embodiment of the process, in which oil having a high oleic acid content is used as the starting material, the organic phase obtained as the product of oxidative cleavage and separated out during step c) substantially comprises pelargonic acid and triglycerides of azelaic, palmitic, stearic and dihydroxystearic acids.

In a preferred embodiment of the process, in which methyl oleate is used as the starting material, the said organic phase substantially comprises pelargonic acid and monomethyl azelate and typically contains methyl palmitate, methyl stearate and methyl dihydroxystearate. The organic phase separated out during step c) advantageously undergoes further separation operations, for example, by feeding it to equipment suitable for separating saturated monocarboxylic acids from saturated carboxylic acids having more than one carboxyl functional group or derivatives thereof. The said separation is advantageously performed by means of distillation and/or evaporation processes. All distillation and/or evaporation processes which do not apply a strong thermal stress to the mixture of products obtained in step b), such as for example distillation in a flow of steam, molecular distillation or evaporation in thin film or falling film evaporators, are preferred.

According to one aspect of the process in which a derivative of the ester type of unsaturated carboxylic acids is fed to step a) as the starting material, the resulting dicarboxylic acid esters (for example, triglycerides of dicarboxylic acids, in the case where the said derivative is a vegetable oil containing unsaturated carboxylic acid triglycerides) can undergo hydrolysis reactions to obtain free saturated dicarboxylic acids.

Advantageously, the process of the invention can be performed batchwise or continuously.

The invention will be illustrated below by means of some examples which are intended to be illustrative and not limiting upon it.

EXAMPLES

Comparative Example 1 (Total Recycling of the Catalyst in Aqueous Phase at pH<4)

Step a)
The following were fed to a reactor fitted with a stirrer and a suitable temperature regulating system:
  1000 g of sunflower oil having a high oleic acid content (82% oleic, 10% linoleic, 4.5% palmitic, 3.5% stearic);
  5 g of tungstic acid (0.7% in moles with respect to the unsaturated carboxylic acid);
  60 g of hydroxylated sunflower oil (intermediate obtained at the end of step a) originating from a previous reaction).

The temperature was brought to 62° C. and 253 cc of a 49.9% solution by weight of $H_2O_2$ was added over 3 hours.

The reaction was carried out under vacuum (absolute pressure of 0.1-0.2 bar) to distil a part of the process water and to prevent excessive dilution of the $H_2O_2$. The gas evaporated was collected and condensed (approximately 127 g of water).

Once the addition of $H_2O_2$ was complete, the reaction was continued at 65° C. for 3 hours. 1.13 kg of an intermediate oxidation product containing vicinal diols was obtained.

Step b)
1130 g of intermediate product obtained in step a) were transferred into a reactor provided with an external recirculating pump.

377 g of a fresh aqueous solution containing 1.5% by weight of cobalt acetate tetrahydrate (0.8% in moles with respect to the diol produced in step a)) was added to the reaction mixture. The pH of the aqueous solution fed in corresponded to 7.3. After mixing with the intermediate product the aqueous phase sampled from the reactor had a pH of 4.3.

The temperature was increased to 72-75° C. and the reactor was raised to a pressure of 25 bar with air. Air flowed continuously, at a throughput of 50 normal liters per minute (Nl/min), to provide a sufficient supply of oxygen. The start of the reaction was detected through the increase in temperature of the mixture as a result of the exothermicity of the oxidative cleavage, and the absorption of oxygen. The quantity of oxygen absorbed was measured using a suitable measuring device (oxygen meter) fitted at the exhaust air discharge.

The reaction ran to completion in approximately 5 hours.
Step (c)
At the end of step b) separation of the aqueous phase from the organic phase was carried out by hot decanting (80° C.) after the addition of 10% by weight of octane.

410 g of aqueous phase was obtained, containing the catalysts from the first two reaction steps and having a pH of 3.2.

After the solvent had been evaporated off from the organic phase, approximately 1181 g of oily product, comprising triglycerides containing mainly azelaic acid (together with smaller quantities of palmitic acid, stearic acid and dihydroxystearic acid) in a mixture with pelargonic acid and free short chain monocarboxylic acids was obtained.

On the basis of gas chromatography analyses of the oily product, the yield from oxidative cleavage in the absence of recycling of the aqueous phase containing the catalyst was 71.5% for pelargonic acid and 70.8% for azelaic acid in comparison with the moles which could be theoretically obtained from the starting oil.

The process was repeated by feeding 1130 g of the intermediate product obtained in step a) to step b), together with 377 g of aqueous phase separated out from step c), (obtained by partial evaporation of the aqueous phase separated out previously, in such a way as to maintain the cobalt acetate tetrahydrate concentration at 1.5%). After mixing with the intermediate product, the aqueous phase sampled from the reactor at the start of step b) had an initial pH of 3.2.

At the end of the oxidative cleavage reaction, the aqueous phase was separated from the oily phase containing the reaction product by hot decanting after the addition of 10% by weight of octane.

On the basis of gas chromatography analysis of the oily product, the yield from oxidative cleavage was 57.8% of pelargonic acid and 61.9% of azelaic acid with respect to the moles which could be theoretically obtained from the starting oil.

As may be seen from the graph in FIG. 2, which shows oxygen absorption in the course of the oxidative cleavage reaction (step b) with recycled catalyst and an initial pH of 3.2, the reaction ran to completion in approximately 7.5 hours.

Example 2 (Total Recycling of the Catalyst in Aqueous Phase at pH>4)

Example 1 was reproduced feeding 377 g of aqueous solution separated out in step c) to step b), but after the addition of 7.5 g of NaOH, so as to bring the pH of the solution to a value of 6.9.

After mixing with the intermediate product, the aqueous phase sampled from the reactor in step b) had an initial pH of 5.2.

The temperature was increased to 72-75° C. and the reactor was raised to a pressure of 25 bar with air. Air flowed continuously (at a throughput of 50 Nl/min) to provide a sufficient supply of oxygen. As may be seen from the graph in FIG. 2, the reaction lasted approximately 5 hours. The reaction time was therefore shorter than that for the process with catalyst recycled without the addition of base and comparable with that of the process carried out using only fresh catalyst.

At the end of step b) the aqueous phase was separated from the organic phase by hot decanting after the addition of 10% by weight of octane.

On the basis of gas chromatography analyses of the oily product, the yield from oxidative cleavage was 74.7% of pelargonic acid and 75.2% of azelaic acid with respect to the moles which could be theoretically obtained from the starting oil.

Comparing the data with that obtained from comparative Example 1, reuse of the aqueous phase containing the catalyst for step b) in the oxidative cleavage reaction as a replacement for fresh catalyst, with a pH of 5.2 at the start of the oxidative cleavage reaction, made it possible to obtain an increase in yield of more than 20% in comparison with reuse with an initial pH of 3.2. The yield was also greater than that obtained using fresh catalyst.

Noteworthy, a further repetition of step b) using the aqueous phase thereby separated (II recycle), after addition of NaOH in order to bring again the pH of the solution to a value of 6.9 and the pH of aqueous phase after mixing with the intermediate product to about 5, allowed again to perform the oxidative cleavage reaction in a reaction time comparable to that of the first recycle (approximately 5 hours). The yield was still comparable to that obtained with the fresh catalyst.

Example 3 (Partial Recycling of the Catalyst in Aqueous Phase at pH>4)

Example 1 was reproduced by feeding 1130 g of intermediate product obtained in step a) to step b) and 377 g of aqueous 1.5% cobalt acetate solution, of which 226 g originated from the aqueous phase separated out in step c) (ratio of 60/40 by weight between the recycled aqueous phase and fresh catalytic solution), after the addition of 4.7 g NaOH in order to bring the pH of the solution to a value of 6.9.

After mixing with the intermediate product the aqueous phase sampled from the reactor had a pH of 4.92.

The temperature was increased to 72-75° C. and the reactor was raised to a pressure of 25 bar with air. Air flowed continuously (at a throughput of 50 Nl/min) to provide a sufficient supply of oxygen. As may be seen from the graph in FIG. 3, the reaction lasted approximately 5 hours. The reaction rate was comparable with that of the process carried out using fresh catalyst.

At the end of the oxidative cleavage reaction the aqueous phase was separated from the organic phase by hot decanting after the addition of 10% by weight of octane.

On the basis of gas chromatography analyses of the oily product, the yield from oxidative cleavage was 73.6% of pelargonic acid and 73.8% of azelaic acid with respect to the moles which could be theoretically obtained from the starting oil. Reusing the aqueous phase containing the catalyst in step b) at 60% by weight and carrying out the oxidative cleavage reaction with an initial pH of 4.92, a yield which was wholly comparable with the reaction carried out using fresh catalyst was obtained.

Comparative Example 4 (Partial Recycling of Catalyst in Aqueous Phase at pH<4)

Example 3 was repeated using an aqueous solution of 1.5% by weight of cobalt acetate tetrahydrate containing 60% by weight of the aqueous phase separated out at the end of step c) of the process and having a pH of 3.6 in step b).

After mixing with the intermediate product containing vicinal diol, the aqueous phase sampled from the reactor had an initial pH of 3.4.

At the end of the oxidative cleavage reaction the aqueous phase was separated from the oily phase containing the reaction product, by hot decanting, after the addition of 10% by weight of octane.

The yield from oxidative cleavage, determined on the basis of gas chromatography analyses of the oily product, was 61.8% of pelargonic acid and 63.9% of azelaic acid in comparison with the moles which could be theoretically obtained from the starting oil.

In comparison with the oxidative cleavage reaction (step b) carried out using fresh catalyst (initial pH 4.3) or with 60% recycled catalyst and an initial pH of 4.92, the reaction with 60% recycled catalyst and an initial pH of 3.4 ran to completion in a time of approximately 2 hours.

The invention claimed is:

1. A process for the oxidative cleavage of unsaturated carboxylic acids and their derivatives for the obtainment of saturated monocarboxylic and dicarboxylic acids or derivatives thereof comprising the steps of:
   a) reacting at least one unsaturated carboxylic acid or derivative thereof, an oxidising compound and a catalyst cap able of catalysing the oxidation reaction of the olefin double bond, in order to obtain an intermediate compound containing vicinal diols, and
   b) reacting the said intermediate compound, oxygen or a compound containing oxygen, and a catalyst capable of catalysing the oxidation reaction of vicinal diols to carboxyl groups in the presence of water, obtaining an organic phase comprising saturated monocarboxylic acids and saturated dicarboxylic acids or their derivatives, and an aqueous phase comprising the said catalyst, and
   c) separating the said aqueous phase from the said organic phase,
   characterised in that at least a part of the said aqueous phase comprising the catalyst and at least one base are fed to step b) so that the mixture of the intermediate compound of step a) with the said part of aqueous phase and the said base has a pH value of between 4 and 7.

2. The process according to claim 1, in which the said derivatives are esters of unsaturated carboxylic acids with monoalcohols and/or polyalcohols.

3. The process according to claim 2 in which the said derivatives are selected from methyl esters, ethyl esters, propyl esters, butyl esters, monoglycerides, diglycerides, triglycerides, or mixtures thereof.

4. The process according to claim 1 in which the said catalyst in step a) is in homogenous or heterogeneous phase and belongs to the group of transition elements and acids, alkali metal salts and complexes thereof.

5. The process according to claim 1 in which the said catalyst in step b) is in homogeneous phase and belongs to the group of transition elements and acids, alkali metal salts and complexes thereof.

6. The process according to claim 1 in which the said catalyst in step b) is selected from Ce, Cr, Co, Cu, Mn, Mo, Re, Os, V and W and acids, alkali metal salts and complexes thereof.

7. The process according to claim 1 in which the said catalyst in step a) is tungstic or phosphotungstic acid, and in which the said catalyst in step b) is a cobalt salt.

8. The process according to claim 1 in which the ratio by weight between the aqueous phase and the organic phase during step b) is below 5:1.

9. The process according to claim 1 in which the reaction time for each of steps a) and b) is between 2 and 8 hours.

10. The process according to claim 1 in which the said step c) comprises one or more operations selected from: decanting, degassing, heating, filtration, washing with water and/or the addition of organic solvents which are immiscible with water.

11. The process according to claim 1 in which the said aqueous phase separated out in step c) is subjected to one or more concentration treatments before being fed back to step b).

12. The process according to claim 1 in which the said base is selected from alkali metal hydroxides, alkaline earth hydroxydes, transition metal hydroxides, alkaline earth oxides, alkaline earth carbonates and bicarbonates, acetates and mixtures thereof.

13. The process according to claim 12 in which the said base is selected from sodium hydroxide and potassium hydroxide.

14. The process according to claim 1 in which the aqueous phase separated out in step c) and comprising the catalyst of step b) is fed back to step b) as an alternative to fresh catalyst.

15. The process according to claim 1 in which the aqueous phase separated out in step c) and comprising the catalyst of step b) is fed back to step b) together with fresh catalyst.

16. The process according to claim 2 in which the said catalyst in step a) is in homogenous or heterogeneous phase and belongs to the group of transition elements and acids, alkali metal salts and complexes thereof.

17. The process according to claim 3 in which the said catalyst in step a) is in homogenous or heterogeneous phase and belongs to the group of transition elements and acids, alkali metal salts and complexes thereof.

18. The process according to claim 2 in which the said catalyst in step b) is in homogeneous phase and belongs to the group of transition elements and acids, alkali metal salts and complexes thereof.

19. The process according to claim 3 in which the said catalyst in step b) is in homogeneous phase and belongs to the group of transition elements and acids, alkali metal salts and complexes thereof.

20. The process according to claim 4 in which the said catalyst in step b) is in homogeneous phase and belongs to the group of transition elements and acids, alkali metal salts and complexes thereof.

* * * * *